United States Patent [19]

Kimura et al.

[11] Patent Number: 5,556,966
[45] Date of Patent: Sep. 17, 1996

[54] PROCESS FOR THE PRODUCTION OF ALUMINUM PHTHALOCYANINE COMPOSITION

[75] Inventors: Shuuichi Kimura; Michichika Hikosaka; Masami Shirao; Akimitsu Mochizuki; Junichi Tsuchida, all of Tokyo, Japan

[73] Assignee: Toyo Ink Manufacturing Co., Ltd., Tokyo, Japan

[21] Appl. No.: 276,660

[22] Filed: Jul. 19, 1994

[30] Foreign Application Priority Data

Jul. 23, 1993 [JP] Japan ................................. 5-182481

[51] Int. Cl.$^6$ ............................................. C09B 67/12
[52] U.S. Cl. .......................... 540/140; 540/122; 540/139; 540/142
[58] Field of Search .......................... 540/140, 138, 540/136, 137

[56] References Cited

U.S. PATENT DOCUMENTS

| 4,311,775 | 1/1982 | Regan | 430/37 |
| 5,282,896 | 2/1994 | Tsuchida | 540/137 |

FOREIGN PATENT DOCUMENTS

| 0047716 | 3/1982 | European Pat. Off. . |
| 879012 | 11/1942 | France . |
| 2504150 | 8/1976 | Germany . |
| 2083815 | 3/1982 | United Kingdom . |

OTHER PUBLICATIONS

Kuroiwa et al., Chemical Abstracts, vol. 106, No. 4, 26 Jan. 1987 Abstract No. 20000k p. 82 JP-A-61-152685.

*Primary Examiner*—Mukund J. Shah
*Assistant Examiner*—Pavanaram K. Sripada
*Attorney, Agent, or Firm*—Wenderoth, Lind & Ponack

[57] ABSTRACT

A process for the production of an aluminum phthalocyanine composition or a halogenated aluminum phthalocyanine composition in high yield and purity is provided which entails bringing a molten salt of aluminum chloride and/or aluminum bromide and a phthalocyanine compound having a central element other than aluminum into contact with each other in a predetermined temperature range thereby to substitute aluminum for the central element. Alternatively, the process involves conducting the aforementioned step, and introducing a halogen into the resultant reaction mixture.

9 Claims, No Drawings

PROCESS FOR THE PRODUCTION OF ALUMINUM PHTHALOCYANINE COMPOSITION

FIELD OF THE INVENTION

The present invention relates to a process for the production of an aluminum phthalocyanine composition or a halogenated aluminum phthalocyanine composition.

PRIOR ART OF THE INVENTION

Aluminum phthalocyanine or halogenated aluminum phthalocyanine is expected to be useful as a pigment or color having a novel hue or as a photoconductive material.

Halogenated aluminum phthalocyanine is thought to be synthesized by any one of the following two methods—one method in which non-halogenated aluminum phthalocyanine is synthesized first and then halogenated to a necessary degree, and the other method in which halogenated aluminum phthalocyanine is synthesized directly from a raw material halogenated in advance. The former method in which halogenated aluminum phthalocyanine is synthesized through two steps has a defect in that the yield of non-halogenated aluminum phthalocyanine in the first step is low, as low as 50% or less, as reported by John P. Linsky, Thomas R. Paul, Ronald S. Hohr and Malcolm E. Kenney report in Inorganic Chem. 19, 3131–3135 (1980). The latter method in which halogenated aluminum phthalocyanine is synthesized directly from a halogenated raw material is disclosed in U.S. Pat. No. 2,549,842 and Zn. Obshch. Khim. 40 (2) 400 (1979), while it is not practically useful since the raw material is expensive. As explained above, there has been no practically useful method for producing halogenated aluminum phthalocyanine.

Meanwhile, JP-A-52-155625 discloses that a trace amount of aluminum hexadecachlorophthalocyanine is formed as a byproduct during a reaction for producing copper hexadecachlorophthalocyanine as an end product by adding copper phthalocyanine into a molten salt of aluminum chloride and then introducing chlorine. In the method disclosed in the above publication, for preventing the formation of an aluminum-substituted byproduct, the temperature at which copper phthalocyanine is added is decreased, and the copper phthalocyanine is added for a short period of time while introducing chlorine. However, when the above reaction is carried out at 190° C., the highest temperature for chlorination, there is obtained no composition having an aluminum phthalocyanine content of at least 50% by weight.

The present inventors have found that there is a particular temperature, which should be called a threshold temperature, at which aluminum phthalocyanine or halogenated aluminum phthalocyanine is efficiently formed by the substitution of a central substance in a molten salt containing aluminum chloride and/or aluminum bromide, and have also found that the substitution proceeds up to a degree depending upon (defined by) a temperature and a central substance even if the temperature is lower than the above particular temperature.

SUMMARY OF THE INVENTION

It is an object of the present invention to provide a process for the production of an aluminum phthalocyanine composition or a halogenated aluminum phthalocyanine composition at high yields with high economic performance.

According to the present invention, there is provided a process for the production of a phthalocyanine composition containing at least 60% by weight of an aluminum phthalocyanine, which comprises the step of bringing a molten salt of aluminum chloride and/or aluminum bromide and a phthalocyanine compound having a central substance other than aluminum into contact with each other in a predetermined temperature range thereby to substitute aluminum for the central substance.

Further, according to the present invention, there is provided a process for the production of a halogenated phthalocyanine composition containing at least 60% by weight of a halogenated aluminum phthalocyanine, which comprises the steps of bringing a molten salt of aluminum chloride and/or aluminum bromide and a phthalocyanine compound having a central substance other than aluminum into contact with each other in a predetermined temperature range thereby to substitute aluminum for the central substance, and introducing a halogen into the resultant reaction mixture.

DETAILED DESCRIPTION OF THE INVENTION

The phthalocyanine compound having a central substance other than aluminum, used in the present invention, includes phthalocyanine compounds containing, as central substances, metals and non-metals such as H, Li, Be, Na, Mg, Si, P, K, Ca, Sc, Ti, V, Cr, Mn, Fe, Co, Ni, Cu, Zn, Ga, Ge, As, Y, Zr, Nb, Mo, Tc, Ru, Rh, Pd, Ag, Cd, In, Sn, Sb, Ba, La, Hf, Ta, W, Re, Os, Ir, Pt, Au, Hg and Lu. As the above phthalocyanine compound, there may be used a phthalocyanine compound in which a halogen atom and/or substituent such as a sulfonic acid group are/is introduced onto the phthalocyanine skeleton.

In the present invention, it has been found that the temperature at which aluminum is substituted for all the central substances of molecules of the phthalocyanine compound has a correlation to the central substance. When the central substance is Co or Ni, the above temperature is 300° C. When the central substance is Fe or Cu, the above temperature is 240° C. When the central substance is Cr or Zn, the above temperature is 140° C. When the central substance is any one of the remaining metals or non-metals, the above temperature is 120° C. The upper limit of the temperature range for the substitution may be, in principle, 400° C. at which phthalocyanine starts to sublimate or higher. Since, however, aluminum chloride or aluminum bromide sublimates vigorously at such a high temperature, it is preferred to set the above upper limit of the temperature range at a temperature which is about 30° C. higher than the temperature at which aluminum is substituted for all the central substances of molecules of the phthalocyanine compound. At a temperature below the above temperature at which aluminum is substituted for all the central substances of molecules of the phthalocyanine compound, the substitution of aluminum proceeds to a degree defined by the central substance and a tempera tulle. When the phthalocyanine compound is a copper phthalocyanine, the substitution proceeds up to 80% at 220° C. and up to 63% at 200° C. The lower limit of the temperature range for the substitution for producing the phthalocyanine composition containing at least 60% by weight of aluminum phthalocyanine differs depending upon the central substance. When the central substance is Fe, the lower limit is 200° C. When the central substance is Co or Ni, the lower limit is 220° C. When the central substance is Cr, Zn or any of the other metals or non-metals, the lower limit is 120° C. The above "lower limit" refers to the lowest temperature at which the molten salt is free from solidification. The phthalocyanine compound and the molten salt of aluminum chloride and/or aluminum bromide are brought into contact at a temperature in the above temperature range (which is defined by the central substance of the phthalocyanine compound) for 0.2 to 80 hours (contact time). Preferably, when the central substance is Ni, the contact time is about 40 hours long. When the central substance is Co, the contact time is about 6 hours long. When the central substance is Fe, Cr or Zn, the contact time is about 1 hour long. When the central substance is any one of the other metals or non-metals, the contact time is about 0.5 hour long. When the contact time is less than the above hours, the yield of aluminum phthalocyanine is low.

In the present invention, a molten salt of aluminum chloride and/or aluminum bromide is used. This salt may be a salt of aluminum chloride alone, or a salt of aluminum bromide alone. Further, the tool ten salt used in the present invention may further contain an alkali metal halide, an alkaline earth metal halide, preferably sodium chloride. In this case, advantageously in operation, the temperature for preparing the molten salt decreases. The amount of the alkali metal halide or the alkaline earth metal salt, preferably sodium chloride, is 0 to 10 parts by weight per 10 parts by weight of the aluminum chloride and/or the aluminum bromide. The molten salt and the phthalocyanine compound are used in such amounts that the aluminum/phthalocyanine compound weight ratio is 50:1 to 2:1, preferably 20:1 to 15:1. When the above ratio is smaller than the above lower limit, there are some cases where it is difficult to proceed with the substitution of aluminum. When the above ratio is larger than the above upper limit, it is disadvantageous in economic performance.

The halogenation in the step of introducing a halogen into the reaction mixture means that the average number of halogen atoms on the phthalocyanine compound after the reaction (introduction) is greater than the average number of halogen atoms on the phthalocyanine compound before the reaction, and that the number of halogen atoms on the phthalocyanine compound is 7 to 16.

The aluminum phthalocyanine referred to in the present invention may be a compound in which phthalocyanine is coordination-bonded to aluminum, and in this compound, another ligand such as a halogen, a hydroxyl group or a nitrate ion, may be bonded to the aluminum. Further, the aluminum phthalocyanine referred to in the present invention may be a direct of aluminum phthalocyanine molecules bonded to each other through oxygen, sulfate ion or phosphate ion.

The aluminum phthalocyanine is halogenated as follows. First, the phthalocyanine compound is subjected to the substitution of aluminum, and while the resultant reaction mixture (molten salt containing aluminum phthalocyanine) is maintained at a temperature between 120° C. and 200° C., a halogen is introduced for 3 to 60 hours. When the above temperature is higher than the above upper limit, the proportion of the halogen to react decreases. When the above temperature is lower than the above lower limit, the molten salt may be solidified. When the above time for the introduction is less than 3 hours, the proportion of the halogen to react decreases, and the amount of heat generated by the reaction heat of the molten salt increases up to a dangerous level. When the above time for the introduction is more than 60 hours, the productivity is low.

The aluminum phthalocyanine or the halogenated aluminum phthalocyanine is obtained as a mixture thereof with the molten salt after the reaction(s). This reaction mixture is poured into a large amount of water, filtered and washed with water to give the aluminum phthalocyanine composition of the present invention.

The present invention will be explained hereinafter with reference to Examples, in which "part" stands for "part by weight" and "%" stands for "% by weight".

Example 1

20 Parts of copper phthalocyanine was dissolved in a molten salt containing 80 parts of aluminum chloride and 20 parts of sodium chloride and having a temperature of 150° C. for a short period of time. The mixture was maintained at 240° C. for 6 hours with stirring. The reaction mixture was poured into 1,000 parts of water. Insolubles were removed by filtration, and the remainder was filtered, washed with water and dried to give 18.8 parts of an aluminum phthalocyanine composition. The composition contained 1.1% of copper phthalocyanine, and the average number of chlorine atoms substituted per phthalocyanine molecule was 0.2.

Comparative Example 1

20 Parts of copper phthalocyanine was dissolved in a molten salt containing 80 parts of aluminum chloride and 20 parts of sodium chloride and having a temperature of 150° C. for a short period of time. The mixture was maintained at 180° C. for 20 hours with stirring. The reaction mixture was poured into 1,000 parts of water. Insolubles were removed by filtration, and the remainder was filtered, washed with water and dried to give 19.4 parts of an aluminum phthalocyanine composition. The composition contained 71.8% of copper phthalocyanine, and the average number of chlorine atoms substituted per phthalocyanine molecule was 0.2.

Example 2

20 Parts of copper phthalocyanine was dissolved in a molten salt containing 80 parts of aluminum chloride and 20 parts of sodium chloride and having a temperature of 150° C. for a short period of time. The mixture was maintained at 240° C. for 6 hours with stirring. Then, while the reaction mixture was maintained at 180° C. with vigorous stirring, chlorine was introduced at a rate of 4 parts/hour for 10 hours. The reaction mixture was poured into 1,000 parts of water. Insolubles were removed by filtration, and the remainder was filtered, washed with water and dried to give 34.2 parts of a chlorinated aluminum phthalocyanine composition. The composition contained 0.9% of chlorinated copper phthalocyanine, and the average number of chlorine atoms substituted per phthalocyanine molecule was 15:1.

Example 3

20 Parts of copper phthalocyanine was dissolved in a molten salt containing 80 parts of aluminum chloride and 20 parts of sodium chloride and having a temperature of 150° C. for a short period of time. The mixture was maintained at 200° C. for 6 hours with stirring. Then, while the reaction mixture was maintained at 180° C. with vigorous stirring, chlorine was introduced at a rate of 4 parts/hour for 10 hours. The reaction mixture was poured into 1,000 parts of water. Insolubles were removed by filtration, and the remainder was filtered, washed with water and dried to give 34.5 parts of a chlorinated aluminum phthalocyanine composition. The composition contained 29.8% of chlorinated copper phthalocyanine, and the average number of chlorine atoms substituted per phthalocyanine molecule was 14.8.

Example 4

20 Parts of copper phthalocyanine was dissolved in a molten salt containing 80 parts of aluminum chloride and 20 parts of sodium chloride and having a temperature of 150° C. for a short period of time. The mixture was maintained at 200° C. for 6 hours with stirring. Then, while the reaction mixture was maintained at 160° C. with vigorously stirring, bromine was dropwise added at a rate of 7.4 parts/hour for 6 hours. Further, while the reaction mixture was maintained at 180° C., chlorine was introduced at a rate of 4 parts/hour for 5 hours. The reaction mixture was poured into 1,000 parts of water. Insolubles were removed by filtration, and the remainder was filtered, washed with water and dried to give 43.2 parts of a halogenated aluminum phthalocyanine composition. The composition contained 31.5% of halogenated copper phthalocyanine, and the average number of bromine atoms substituted per phthalocyanine molecule was 7.2.

Example 5

20 Parts of copper phthalocyanine was dissolved in a molten salt containing 40 parts of aluminum chloride, 77 parts of aluminum bromide and 20 parts of sodium chloride and having a temperature of 150° C. for a short period of time. The mixture was maintained at 200° C. for 6 hours with stirring. The reaction mixture was poured into 1,000 parts of water. Insolubles were removed by filtration, and the remainder was filtered, washed with water and dried to give 19.0 parts of an aluminum phthalocyanine composition. The composition contained 29.2% of copper phthalocyanine, and the average number of chlorine atoms substituted per phthalocyanine molecule was 0.1.

Example 6

20 Parts of cobalt phthalocyanine was dissolved in a molten salt containing 80 parts of aluminum chloride and 20 parts of sodium chloride and having a temperature of 150° C. for a short period of time. The mixture was maintained at 310° C. for 20 hours with stirring. The reaction mixture was poured into 1,000 parts of water. Insolubles were removed by filtration, and the remainder was filtered, washed with water and dried to give 18.3 parts of an aluminum phthalocyanine composition. The composition contained 1.6% of cobalt phthalocyanine, and the average number of chlorine atoms substituted per phthalocyanine molecule was 1.8.

Example 7

20 Parts of nickel phthalocyanine was dissolved in a molten salt containing 80 parts of aluminum chloride and 20 parts of sodium chloride and having a temperature of 150° C. for a short period of time. The mixture was maintained at 310° C. for 40 hours with stirring. The reaction mixture was poured into 1,000 parts of water. Insolubles were removed by filtration, and the remainder was filtered, washed with water and dried to give 18.0 parts of an aluminum phthalocyanine composition. The composition contained 2.9% of nickel phthalocyanine, and the average number of chlorine atoms substituted per phthalocyanine molecule was 2.3.

Example 8

20 Parts of iron phthalocyanine was dissolved in a molten salt containing 80 parts of aluminum chloride and 20 parts of sodium chloride and having a temperature of 150° C. for a short period of time. The mixture was maintained at 240° C. for 1 hour with stirring. The reaction mixture was poured into 1,000 parts of water. Insolubles were removed by filtration, and the remainder was filtered, washed with water and dried to give 18.3 parts of an aluminum phthalocyanine composition. The composition contained 0.6% of iron phthalocyanine, and the average number of chlorine atoms substituted per phthalocyanine molecule was 0.2.

Example 9

20 Parts of iron phthalocyanine was dissolved in a molten salt containing 80 parts of aluminum chloride and 20 parts of sodium chloride and having a temperature of 150° C. for a short period of time. The mixture was maintained at 240° C. for 2 hours with stirring. Then, while the reaction mixture was maintained at 180° C. with vigorous stirring, chlorine was introduced at a rate of 4 parts/hour for 10 hours. The reaction mixture was poured into 1,000 parts of water. Insolubles were removed by filtration, and the remainder was filtered, washed with water and dried to give 32.7 parts of a chlorinated aluminum phthalocyanine composition. The composition contained 0.9% of chlorinated iron phthalocyanine, and the average number of chlorine atoms substituted per phthalocyanine molecule was 14.9.

Example 10

20 Parts of zinc phthalocyanine was dissolved in a molten salt containing 80 parts of aluminum chloride and 20 parts of sodium chloride and having a temperature of 150° C. for a short period of time. The mixture was maintained at 150° C. for 1 hour with stirring. The reaction mixture was poured into 1,000 parts of water. Insolubles were removed by filtration, and the remainder was filtered, washed with water and dried to give 18.7 parts of an aluminum phthalocyanine composition. The composition contained 2.0% of zinc phthalocyanine, and the average number of chlorine atoms substituted per phthalocyanine molecule was 0.3.

Example 11

20 Parts of zinc phthalocyanine was dissolved in a molten salt containing 160 parts of aluminum bromide and 20 parts of sodium chloride and having a temperature of 150° C. for a short period of time. The mixture was maintained at 150° C. for 1 hour with stirring. The reaction mixture was poured into 1,000 parts of water. Insolubles were removed by filtration, and the remainder was filtered, washed with water and dried to give 18.8 parts of an aluminum phthalocyanine composition. The composition contained 1.8% of zinc phthalocyanine, and the average number of bromine atoms substituted per phthalocyanine molecule was 0.1.

Example 12

20 Parts of chromium phthalocyanine was dissolved in a molten salt containing 80 parts of aluminum chloride and 20 parts of sodium chloride and having a temperature of 150° C. for a short period of time. The mixture was maintained at 150° C. for 1 hour with stirring. The reaction mixture was poured into 1,000 parts of water. Insolubles were removed by filtration, and the remainder was filtered, washed with water and dried to give 19.4 parts of an aluminum phthalocyanine composition. The composition contained 0.8% of chromium phthalocyanine, and the average number of chlorine atoms substituted per phthalocyanine molecule was 0.9.

Examples 13–25

20 Parts of a phthalocyanine compound shown in Table 1 was dissolved in a molten salt containing 80 parts of aluminum chloride and 20 parts of sodium chloride and having a temperature of 150° C. for a short period of time. The mixture was maintained at 150° C. for 1 hour with stirring. The reaction mixture was poured into 1,000 parts of water. Insolubles were removed by filtration, and the remainder was filtered, washed with water and dried to give an aluminum phthalocyanine composition. Table 1 shows phthalocyanine compounds used, yields and purifies [content (%) of aluminum phthalocyanine in the composition] of aluminum phthalocyanine compositions produced and the average numbers of chlorine atoms substituted per phthalocyanine molecule.

TABLE 1

| Ex. | Phthalocyanine compound | Yield (part) | Purity (%) | Average number of chlorine atoms per phthalocyanine molecule |
|---|---|---|---|---|
| 13 | Phthalocyanine | 20.1 | 97.8 | 0.2 |
| 14 | Dilithium Pc | 20.5 | 98.9 | 0.2 |
| 15 | Sodium Pc | 20.2 | 98.2 | 0.2 |
| 16 | Magnesium Pc | 20.0 | 96.8 | 0.2 |
| 17 | Dichlorosilicon Pc | 17.3 | 98.5 | 0.2 |
| 18 | Vanadium oxide Pc | 17.8 | 97.3 | 0.2 |
| 19 | Manganese Pc | 18.1 | 96.8 | 0.2 |
| 20 | Yttrium Pc | 17.0 | 96.4 | 0.2 |
| 21 | Palladium Pc | 16.8 | 97.0 | 0.2 |
| 22 | Silver Pc | 16.6 | 95.8 | 0.2 |
| 23 | Tin Pc | 16.1 | 98.4 | 0.2 |
| 24 | Lead Pc | 14.0 | 95.1 | 0.2 |
| 25 | Ruthenium diacetate Pc | 12.0 | 88.7 | 0.2 |

Notes:
Ex. = Example,
Pc = phthalocyanine

As explained above, according to the present invention, an aluminum phthalocyanine can be produced from a phthalocyanine compound having a central substance other than aluminum at high yields, at least 60% by weight, further as high as 90% by weight or more. When a copper phthalocyanine which is mass-produced as a pigment in industry is used as a raw material, an aluminum phthalocyanine can be produced advantageously in economic performance.

What is claimed is:

1. A process for the production of a phthalocyanine composition containing less than 40% by weight of a phthalocyanine compound having as a central element at least one element selected from H, Li, Be, Na, Mg, Si, K, Ca, Sc, Ti, V, Cr, Mn, Fe, Co, Ni, Cu, Zn, Ga, Ge, As, Y, Zr, Nb, Mo, Pd, Ag, Sn, Pb and Ru and at least 60% by weight of an aluminum phthalocyanine, the process comprising bringing a phthalocyanine compound having as a central element at least one element selected from H, Li, Be, Na, Mg, Si, K, Ca, Sc, Ti, V, Cr, Mn, Fe, Co, Ni, Cu, Zn, Ga, Ge, As, Y, Zr, Nb, Mo, Pd, Ag, Sn, Pb and Ru and a molten salt of aluminum chloride or aluminum bromide into contact with each other at a temperature of at least 220° C. when the phthalocyanine compound has at least one of Cu, Co and Ni as a central element, at a temperature of at least 200° C. when the phthalocyanine compound has Fe as a central element, or at a temperature of at least 120° C. when the phthalocyanine compound has at least one of H, Li, Be, Na, Mg, Si, K, Ca, Sc, Ti, V, Cr, Mn, Fe, Co, Ni, Cu, Zn, Ga, Ge, As, Y, Zr, Nb, Mo, Pd, Ag, Sn, Pb and Ru as a central element, thereby substituting aluminum for the central element.

2. A process according to claim 1, wherein the temperature at which the phthalocyanine compound and the molten salt are brought into contact with each other is in a temperature range not exceeding 400° C.

3. A process according to claim 1, wherein the temperature at which the phthalocyanine compound and the molten salt are brought into contact with each other is 240° C. or higher when the phthalocyanine compound has Fe or Cu as a central element.

4. A process according to claim 1, wherein the molten salt further contains an alkali metal halide or an alkaline earth metal halide.

5. A process according to claim 1, wherein the molten salt further contains an alkali metal halide or an alkaline earth metal halide in an amount of up to 10 parts by weight per 10 parts by weight of the aluminum chloride or the aluminum bromide.

6. A process according to claim 1, wherein the phthalocyanine compound in an amount of 2 to 50 parts by weight per 100 parts by weight of the molten salt, and the molten salt are brought into contact with each other.

7. A process for the production of a phthalocyanine composition containing less than 40% by weight of a phthalocyanine compound having as a central element at least one element selected from H, Li, Be, Na, Mg, Si, K, Ca, Sc, Ti, V, Cr, Mn, Fe, Co, Ni, Cu, Zn, Ga, Ge, As, Y, Zr, Nb, Mo, Pd, Ag, Sn, Pb and Ru and at least 60% by weight of an aluminum phthalocyanine, the process comprising bringing a phthalocyanine compound having as a central element at least one element selected from H, Li, Be, Na, Mg, Si, K, Ca, Sc, Ti, V, Cr, Mn, Fe, Co, Ni, Cu, Zn, Ga, Ge, As, Y, Zr, Nb, Mo, Pd, Ag, Sn, Pb and Ru and a molten salt of aluminum chloride or aluminum bromide into contact with each other at a temperature of at least 220° C. when the phthalocyanine compound has at least one of Cu, Co and Ni as a central element, at a temperature of at least 200° C. when the phthalocyanine compound has Fe as a central element, or at a temperature of at least 120° C. when the phthalocyanine compound has at least one of H, Li, Be, Na, Mg, Si, K, Ca, Sc, Ti, V, Cr, Mn, Fe, Co, Ni, Cu, Zn, Ga, Ge, As, Y, Zr, Nb, Mo, Pd, Ag, Sn, Pb and Ru as a central element, thereby substituting aluminum for the central element, and introducing a halogen into the resultant reaction mixture.

8. A process according to claim 7, wherein the halogenated phthalocyanine has 7 to 16 halogen atoms substituted per molecule of the halogenated phthalocyanine.

9. A process according to claim 7, wherein the halogen is introduced while the reaction mixture is maintained at a temperature in the range of from 120° C. to 200° C.

* * * * *